(12) United States Patent
Suzuki et al.

(10) Patent No.: US 6,239,600 B1
(45) Date of Patent: May 29, 2001

(54) MICROWAVE TYPE CONCENTRATION MEASURING APPARATUS

(75) Inventors: Etsumi Suzuki, Saitama-ken; Seiji Yamaguchi, Kanagawa-ken, both of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/150,699

(22) Filed: Sep. 10, 1998

(30) Foreign Application Priority Data

Sep. 11, 1997 (JP) .................................................. 9-246923

(51) Int. Cl.[7] .................................................. G01R 27/32
(52) U.S. Cl. ............................................ 324/637; 324/639
(58) Field of Search .................................... 324/637, 639, 324/640, 632, 76.52; 73/601, 602

(56) References Cited

U.S. PATENT DOCUMENTS

| | | | |
|---|---|---|---|
| 4,764,718 | * | 8/1988 | Revus et al. .......................... 324/640 |
| 4,962,384 | * | 10/1990 | Walker ................................. 324/786 |
| 5,502,393 | * | 3/1996 | Yamaguchi et al. ................... 324/639 |
| 5,581,191 | | 12/1996 | Yamaguchi . |
| 5,610,527 | | 3/1997 | Yamaguchi . |

* cited by examiner

*Primary Examiner*—Safet Metjahic
*Assistant Examiner*—T. R. Sundaram
(74) *Attorney, Agent, or Firm*—Finnegan, Henderson, Farabow, Garrett & Dunner, L.L.P.

(57) ABSTRACT

The present invention finds the overall concentration of a mixture in the following way. It measures the measurement sensitivity of substance C, of which the constituent composition varies, out of multiple substances A, B and C using sensitivity measuring microwave type concentration meter 17. It then inputs this measurement result to calibration curve gradient setter 20. It then finds the calibration curve gradient using a computing device which possesses the relationship of the measurement sensitivity of the single substance of which the constituent composition varies to the calibration curve gradient that finds the overall concentration of substances A, B and C. It then sets this calibration curve gradient in mixture concentration measuring microwave type concentration meter 18. Then, based on the setting of this gradient, it finds phase difference $\Delta\theta=(\theta 2-\theta 1)$ from phase lag $\theta 1$ of microwaves which are diffused by a reference liquid and phase lag $\theta 2$ of microwaves dispersed by the mixture. At the same time, it finds the overall concentration of the mixture using the calibration curve ($=a\Delta\theta+b$) corresponding to the mixture.

4 Claims, 4 Drawing Sheets

MICROWAVE TYPE CONCENTRATION MEASURING APPARATUS

BACKGROUND OF THE INVENTION

1. Field of the Invention

The present invention relates to microwave type concentration measuring apparatus that measures the concentrations of fluid bodies to be measured which contain various suspended solids or soluble substances, such as sewage sludge, pulp or building materials.

2. Description of the Related Art

Hitherto, as equipment for measuring the concentrations of suspended solids and the like, ultrasonic type concentration meters, which find the concentration by measuring the attenuation factor of ultrasonic waves, and optical type concentration meters, which find the concentration using light by measuring the attenuation factor of transmitted light or the increase of scattered light, have been widely used.

However, with ultrasonic type concentration meters, if, for example, bubbles are intermixed in the fluid, these have a great effect and there are large measurement errors. Also, with optical type concentration meters, if dirt or the like adheres to the optical windows used for projecting the light or receiving the light, this, too, has a great effect and there are large measurement errors.

Therefore, recently, as a concentration meter which does not undergo these influences of bubbles in the fluid and dirt on optical windows, a microwave type concentration measuring apparatus has been conceived and is about to be put into practical use.

FIG. 1 shows a schematic block diagram of this type of microwave type concentration measuring apparatus. This is composed as follows. The microwave transmitting antenna 2 and the microwave receiving antenna 3 are located opposite each other and are attached on the outside wall of pipe 1 which contains the flowing fluid to be measured. The microwaves pass through the fluid to be measured which is flowing in pipe 1. Microwaves from microwave generator 4 are inputted to microwave transmitting antenna 2 via power splitter 5. The microwaves transmitted from microwave transmitting antenna 2 are diffused in the fluid under measurement inside pipe 1, received by microwave receiving antenna 3 and inputted to phase difference measuring circuit 6. At the same time, microwaves from microwave generator 4 are directly inputted to phase difference measuring circuit 6 via power splitter 5. Then, phase lag $\theta 2$ of the microwaves coming diffused by the fluid under measurement in pipe 1 behind the microwaves directly transmitted from microwave generator 4 via power splitter 5 is found by this phase difference measuring circuit 6. Next, this phase lag $\theta 2$ is compared with phase lag $\theta 1$, which is that measured beforehand by filling pipe 1 with a reference fluid (for example, tap water, which can be regarded as zero concentration) and measuring the microwaves coming diffused by the reference fluid in the same state as the fluid under measurement. The design is to find the concentration X of the fluid under measurement from the resulting phase difference $\Delta\theta=(\theta 2-\theta 1)$ using a calibration curve such as that shown in FIG. 2. This concentration X can be found based on calibration curves of $X=a\Delta\theta+b$ corresponding to each type of fluid under measurement. Here, a is the gradient of the calibration curve, and b is the intercept. Normally, b=0.

When using this type of microwave type concentration measuring apparatus, the phase difference of the microwaves is measured, not the attenuation factor. Also, there is no need for any windows through which the microwaves are projected and received to be transparent. Therefore, the measurement apparatus is not easily affected by bobbles or dirt, making it possible to continuously measure the concentration of the fluid under analysis.

However, in a case such as a fluid under measurement containing a number of substances, if the constituent composition of one of these substances should vary, the measurement sensitivity would change due to the effect of that. Thus there were times when errors which could not be ignored occurred in concentration measurement results for fluids under measurement.

Now, for example, consider the case of mixture concentration measurement of a fluid under measurement in a state in which a compound, in which substances A, B and C are mixed in constant proportions, is suspended in water. If it is taken that the constituent (molecules and elements) composition of substances A and B do not vary but the constituent composition of substance C does vary, the variation of the constituent composition of that substance C will produce a great effect on the measurement sensitivity of the mixture of substances A, B and C as a whole. For example, when simple carbon is contained in substance C and the percentage content of that carbon varies, that variation will appear as a variation of the measurement sensitivity of the mixture as a whole.

Also, if the measurement sensitivity of the mixture as a whole varies, errors will occur in the results of concentration measurement of the fluid under measurement. The reason for that can be considered as the following.

Here, for the measurement sensitivity of a microwave type concentration measuring apparatus that uses the phase difference measurement method, by how much the phase difference varies for a 1% concentration (weight %) variation when expressed by an equation becomes:

Measurement sensitivity=(Phase difference $\Delta\theta$)/(Concentration $X$)=(1/a)

and is expressed by the inverse of gradient a of the calibration curve. Here, intercept b of the calibration curve=0.

By this means, if the measurement sensitivities of substances A, B and C as respective simple bodies are taken as ($1$/a1), (1/a2) and (1/a3), measurement sensitivity (1/a0) of the mixture as a whole is determined by (1/a1), (1/a2) and (1/a3) and the mixture proportions of substances A, B and C. Therefore, supposing that measurement sensitivity (1/a3) varies due to variation of the constituent composition of substance C, measurement sensitivity (1/a0) of the mixture as a whole will also vary. In this case, if correction is not carried out by taking the constituent composition of substance C at the time of a certain state as a reference, concentration measurement errors will occur.

SUMMARY OF THE INVENTION

Accordingly, one object of the present invention is to provide a novel microwave type concentration measuring apparatus which has been devised in the light of the above facts and can always perform accurate concentration measurement.

The above object of the present invention can be achieved by providing a microwave type concentration measuring apparatus having the following composition. That is to say, in a microwave type concentration measuring apparatus designed to find the concentration of mixture as a whole by finding the phase difference of the two phase lags from a first phase lag of microwaves which have been diffused by a reference liquid and a second phase lag of microwaves which have been diffused by a mixture prepared by mixing multiple substances and a liquid in constant proportions and using a calibration curve having a gradient corresponding to the mixture based on this phase difference, measuring the measurement sensitivity of an individual substance, of which the constituent composition varies, out of the multiple substances and, at the same time, setting the gradient of the calibration curve which corresponds to the mixture as a whole based on those measurement results.

By this means, in the overall concentration measurement of a mixture which has been mixed from multiple substances, even if the measurement sensitivity varies due to variation of the constituent composition of one individual substance out of these, concentration measurement can be performed without undergoing any effect from that.

The above object of the present invention can also be achieved by providing a microwave type concentration measuring apparatus having the following composition. That is to say, in the above-mentioned invention, providing a calibration curve gradient setting device that possesses a computing device which calculates the relationship of the calibration curve gradient for finding the concentration of a mixture composed of multiple substances with the measurement sensitivity of an individual substance of which the constituent composition varies;

finding the calibration curve gradient by the computing device of the calibration curve gradient setting device based on the measurement result for the measurement sensitivity of the individual substance of which the constituent composition varies and setting this calibration curve gradient.

By this means, the calibration curve gradient is updated every time a measurement result of the measurement sensitivity of the individual substance is inputted, and the most recent curve setting state is maintained.

Therefore highly accurate concentration measurement can be continuously performed.

Moreover, the above object of the present invention can also be achieved by providing a microwave type concentration measuring apparatus with the following composition. That is to say, in the above-mentioned invention, further providing a time lag setting device that inputs to the calibration curve gradient setting device by delaying for a specified time the measurement result for the measurement sensitivity of the individual substance of which the constituent composition varies.

By this means, with a calibration curve gradient based on the result of the measurement time for the measurement sensitivity of the individual substance of which the constituent composition varies, a concentration of the mixture equivalent to this time of measurement can be measured.

Therefore overall concentration measurement of a mixture, composed by a method such as mixing multiple substances, can be continuously performed with good accuracy.

Furthermore, the above object of the present invention can also be achieved by providing a microwave type concentration measuring apparatus having the following composition. That is to say, in the said invention, further providing an averaging device which inputs to the calibration curve gradient setting device mean values of the measurement sensitivity of the individual substance of which the constituent composition varies.

By this means, the mean value of the measurement sensitivity of the individual substance of which the constituent composition varies is used in setting the calibration curve gradient. Therefore, by performing the mixing of multiple substances in batch style, the concentration measurement of the whole of mixtures of types such as supplied to production processes batch by batch can be performed with good accuracy.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
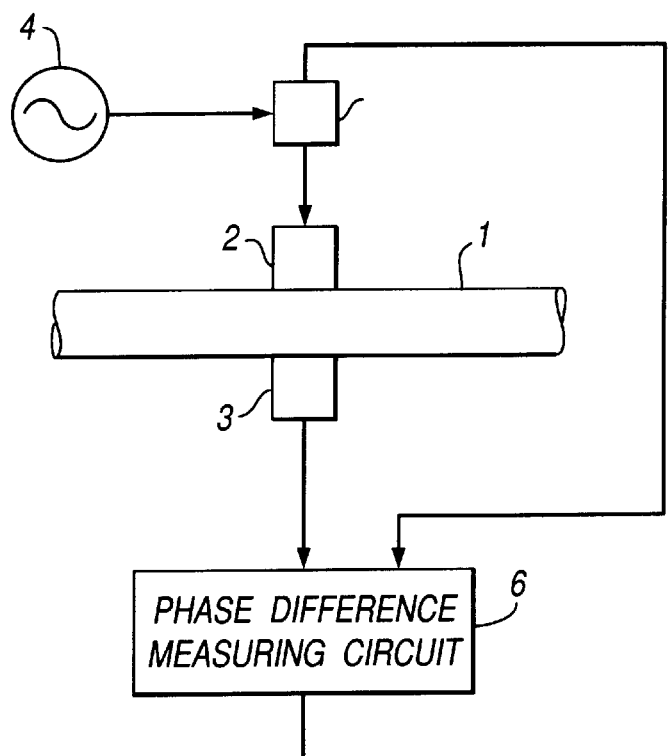
FIG. 1 is a drawing showing a schematic composition of a prior art microwave type concentration measuring apparatus.
Figure 2:
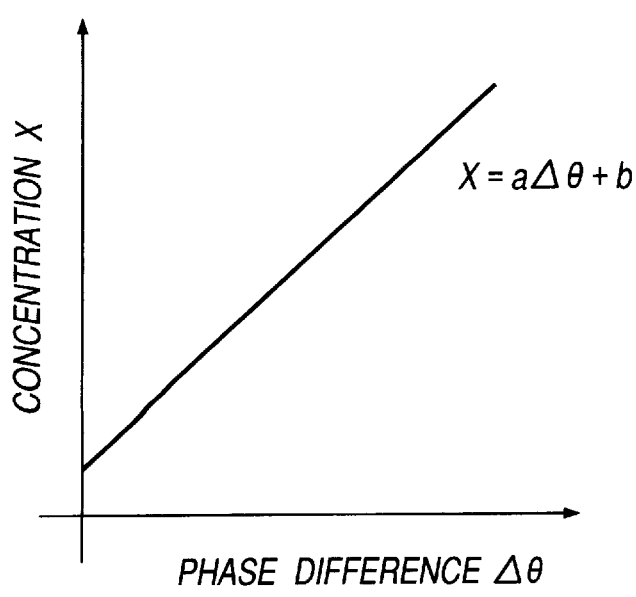
FIG. 2 is a drawing showing a calibration curve used in a prior art microwave type concentration measuring apparatus.

Referring now to the drawings, wherein like reference numerals designate identical or corresponding parts throughout the several views, and more particularly to FIG. 3 thereof, one embodiment of the present invention will be described.

(Embodiment 1)

Figure 3:
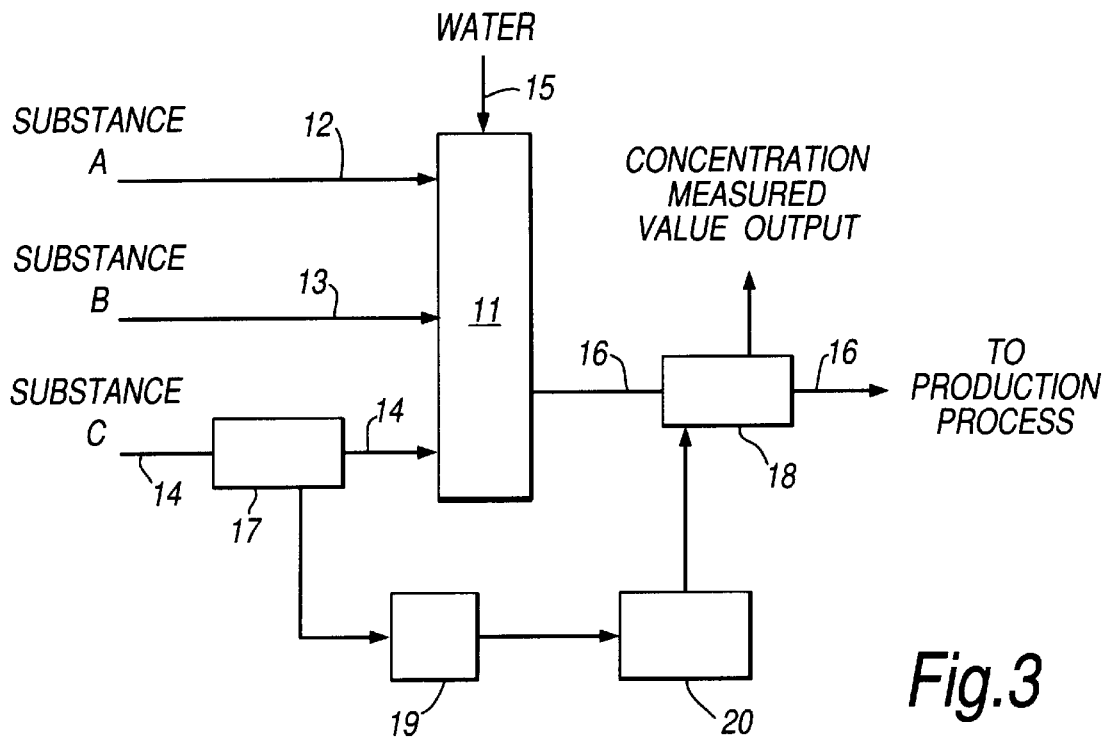
FIG. 3 is a drawing showing the schematic composition of a first embodiment of the present invention.

FIG. 3 shows the schematic composition of a microwave type concentration measuring apparatus in which the present invention is applied. This shows an example of the application of the present invention to a process for producing some product or other, taking a mixture of substances A, B and C in constant proportions suspended in water as the feedstock. Also, here, it is taken that the constituent (molecules and elements) compositions of substances A and B do not vary, but that the constituent composition of substance C does vary. It is also taken that this variation of the constituent composition of substance C has a great influence on the measurement sensitivity of the mixture of substances A, B and C as a whole. For example, this is a case where carbon is contained in substance C, the percentage content of that carbon varies, and that variation appears as a variation of the measurement sensitivity of the mixture as a whole.

In the drawing, 11 is the substance mixing unit. Substance A supply pipe 12, which supplies substance A, substance B supply pipe 13, which supplies substance B, substance C supply pipe 14, which supplies substance C at a constant concentration, and water supply pipe 15, which supplies water, are connected to substance mixing unit 11. The design is to prepare a mixture by mixing these substances A, B and C, which are supplied by substance A supply pipe 12, substance B supply pipe 13 and substance C supply pipe 14 in constant proportions together with water, which is supplied from water supply pipe 15. Also, the design is to supply the mixture mixed in substance mixing unit 11 to a production process (not illustrated) as a feedstock via mixed fluid pipe 16.

Microwave type concentration meter 17, for sensitivity measurement, is mounted on substance C supply pipe 14. Also, microwave type concentration meter 18, for mixture concentration measurement, is mounted on mixture fluid pipe 16.

Sensitivity measuring microwave type concentration meter 17 measures the measurement sensitivity of substance C through substance C supply pipe 14.

Also, mixture concentration measuring microwave type concentration meter 18 is storing reference fluid (normally water) lag delay $\theta 1$, which has been previously measured as mentioned above. It finds phase difference $\Delta\theta=(\theta 2-\theta 1)$ between phase lag $\theta 1$ and phase lag $\theta 2$ of the microwaves which are diffused through the mixture of substances A, B and C flowing through mixture fluid pipe 16. Then it multiplies this phase difference $\Delta\theta$ by calibration curve gradient a0, which corresponds to the measurement sensitivity of substance C that passed through sensitivity measuring microwave type concentration meter 17 at time T earlier, which has been set by calibration curve gradient setter 20 (mentioned below), and finds mixture fluid concentration X ($=a0*\Delta\theta$). It then outputs this as the concentration measured value.

Mixture fluid concentration measuring microwave type concentration meter 18 is connected to sensitivity measuring microwave type concentration meter 17 via time lag setter 19 and calibration curve gradient setter 20.

Time lag setter 19 finds in advance the time T that substance C, which has passed sensitivity measuring microwave type concentration meter 17, will take to reach mixture fluid concentration measuring microwave type concentration meter 18, having been mixed with the other substances A and B and water in substance mixer unit 11 and passed along mixture fluid pipe 16. It then sets this time T.

Also, calibration curve gradient setter 20 sets the calibration curve gradient of mixture concentration measuring microwave type concentration meter 18. Calibration curve gradient setter 20 is provided with a computing device that calculates the relationship between the measurement sensitivity of the single substance of which the constituent composition varies (here, substance C) and the gradient of the calibration curve that finds the concentration of the mixture of substances A, B and C as a whole. It is designed to be able to find the gradient of the calibration curve using the computing device in response to input signals due to the measurement results of sensitivity measuring microwave type concentration meter 17 for substance C by itself, and to set this calibration curve gradient in mixture concentration measuring microwave type concentration meter 18.

Figure 4:
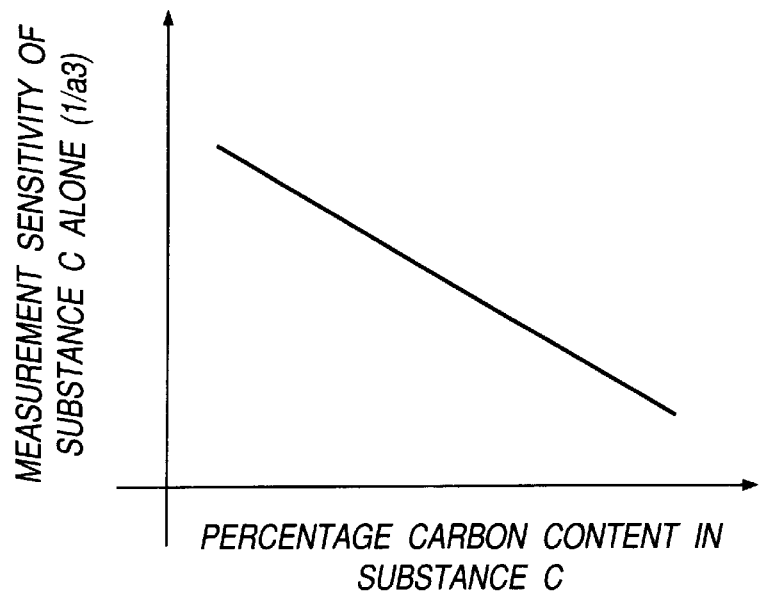
FIG. 4 is a drawing showing an example of the relationship between the percentage carbon content in substance C by itself and the measurement sensitivity of substance C for the first embodiment.
Figure 5:
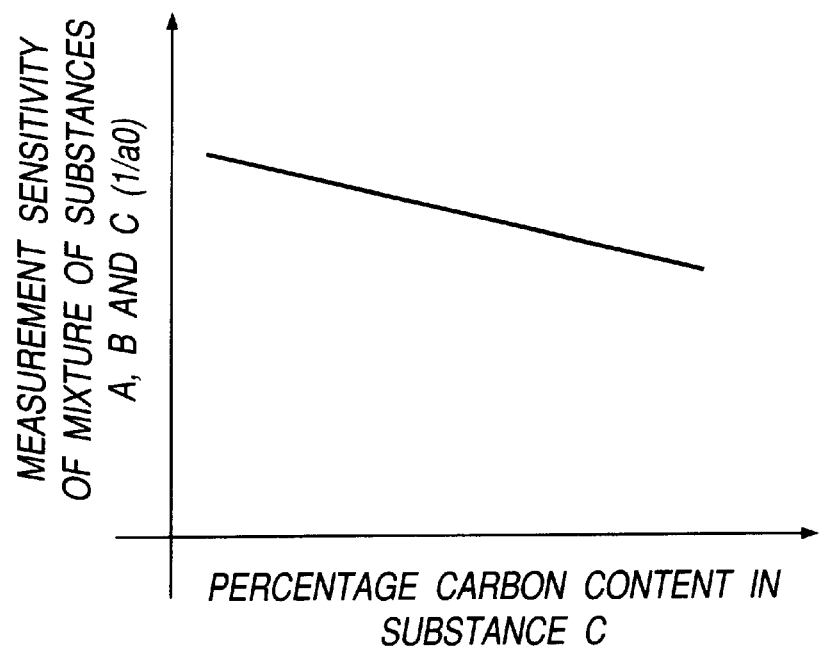
FIG. 5 is a drawing showing an example of the relationship between the percentage carbon content of substance C and the mixture measurement sensitivity of substances A, B and C for the first embodiment.
Figure 6:
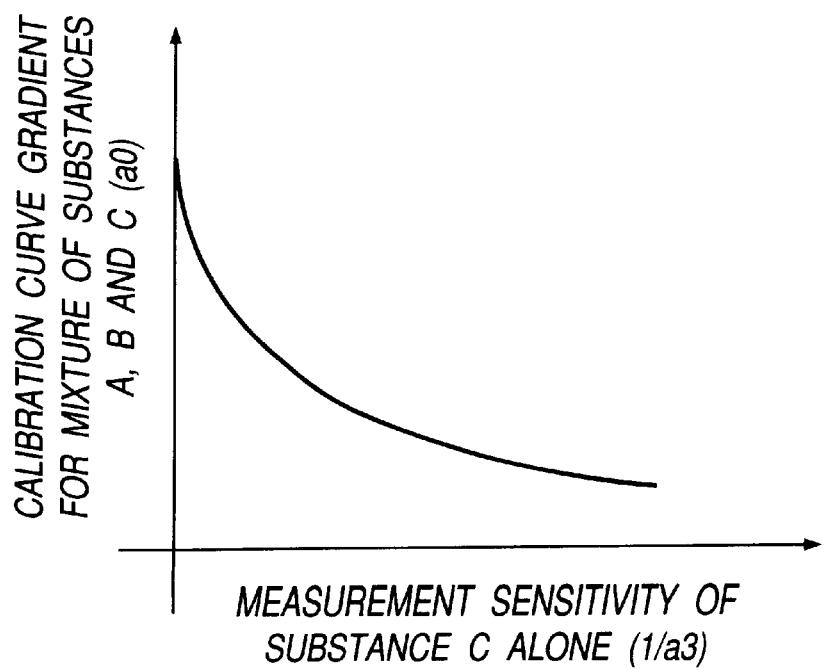
FIG. 6 is a drawing showing an example of the relationship between the measurement sensitivity of substance C by itself and the gradient of the calibration curve for the mixture of substances A, B and C for the first embodiment.

In practice, first it finds measurement results, such as shown in FIG. 4, by measuring beforehand using a microwave type concentration meter or the like how the measurement sensitivity ($1/a3$) of substance C, which contains simple carbon (of which the percentage content varies) varies due to its percentage carbon content. Next, it prepares multiple varieties of mixtures of substances A, B and C, in which substances A and B and substance C with differing percentage carbon contents are combined. Then it measures beforehand using a microwave type concentration meter or the like how the measurement sensitivity ($1/a0$) of the mixture of substances A, B and C varies due to the percentage carbon content of substance C, and obtains measurement results such as shown in FIG. 5. It is designed then to find, from these relationships in FIG. 4 and FIG. 5, the relationship between the measurement sensitivity ($1/a3$) of substance C and the gradient (a0) of the calibration curve which finds the concentration of the mixture of substances A, B and C, as shown in FIG. 6. Then, having prepared a computing device possessing such a relational expression, it is designed to be able to find calibration curve gradient (a0) corresponding to the measured value input of sensitivity measuring microwave type concentration meter 17 for substance C, and to set this calibration curve gradient in mixture concentration measuring microwave type concentration meter 18.

The following is a description of the schematic composition of an embodiment composed in this way.

First, substances A, B and C and water are supplied in set proportions to substance mixing unit 11 via substance A supply pipe 12, substance B supply pipe 13, substance C supply pipe 14 and water supply pipe 15. In this case, substance C, of which the constituent composition varies, is supplied in a state in which it is suspended in water at a constant concentration.

Then, a mixture is prepared by substance mixing unit 11 in which substances A, B and C and water are uniformly mixed. This mixture is supplied as feedstock to a production process (not illustrated) via mixed fluid supply pipe 16.

From this state, when the measurement sensitivity of substance C passing through substance C supply pipe 14 is measured by sensitivity measuring microwave type concentration meter 17 mounted on substance C supply pipe 14, that measurement sensitivity is sent to time lag setter 19. Here, it is delayed by pre-set time T and then inputted to calibration curve gradient setter 20.

Then, in calibration curve gradient setter 20, the calibration curve gradient corresponding to the inputted substance C measurement sensitivity is calculated by a computing device, based on the relational expression between the measurement sensitivity ($1/a3$) of substance C and the calibration curve gradient (a0) that finds the mixed substance concentration of substances A, B and C. This calibration curve gradient is then set in mixed substance concentration measuring microwave type concentration meter 18.

By this means, the phase difference $\Delta\theta=(\theta 2-\theta 1)$ is found by mixture concentration measuring microwave type concentration meter 18 from phase lag $\theta 2$ of microwaves which are diffused in the mixture of substances A, B and C flowing in mixed fluid supply pipe 16 and pre-set and stored phase lag $\theta 1$ of a reference fluid (normally water). Next, mixture concentration X ($=a0*\Delta\theta$) is found. This is the gradient (a0) of the calibration curve corresponding to the measurement sensitivity of substance C that passed through sensitivity measuring microwave type concentration meter 17 at time T earlier and was set by calibration curve gradient setter 20 multiplied by this phase difference $\Delta\theta$. This concentration X is then outputted as the concentration measured value.

Consequently, when this is done, the measurement sensitivity of substance C by itself, of which the constituent composition varies, out of multiple substances A, B and C is measured by sensitivity measuring microwave type concentration meter 17. This sensitivity measurement result is inputted to calibration curve gradient setter 20, and the curve gradient is found by a computing device that possesses the relational expression between the measurement sensitivity of the single substance of which the constituent composition varies and the gradient of the calibration curve which finds the concentration of the mixture of substances A, B and C as a whole. This found calibration curve gradient is set in mixture concentration measuring microwave type concentration meter 18. The design is that, based on this set gradient, the phase difference $\Delta\theta=(\theta2-\theta1)$ is found from phase lag $\theta1$ of the microwaves diffused by the reference fluid and phase lag $\theta2$ of the microwaves diffused by the mixture. Together with this, the concentration of the mixture as a whole is found by the calibration curve $(=a\Delta\theta+b)$ corresponding to the mixture. Therefore, in the overall concentration measurement of a mixture mixed from multiple substances, even in the case of variation of the constituent composition of one single substance out of these, concentration measurement can be accurately performed without being affect by that variation. Also, the gradient of the calibration curve of mixture concentration measuring microwave type concentration meter 18 is refreshed every time the result of measurement of the measurement sensitivity of substance C alone by sensitivity measuring microwave type concentration meter 17 is inputted by the computing device of calibration curve gradient setter 20. Therefore, since the most recent gradient setting state is maintained, highly accurate concentration measurement can be continuously performed.

Also, the design is that the input to calibration curve gradient setter 20 of the measurement result of sensitivity measuring microwave type concentration meter 17 is delayed by time lag setter 19 by the time T until substance C that has passed sensitivity measuring microwave type concentration meter 17 is mixed with the other substances A and B and water in substance mixing unit 11 and reaches mixture concentration measuring microwave type concentration meter 18 by passing through mixed fluid supply pipe 16. Thus the concentration of the mixture equivalent to a measurement time that uses a calibration curve gradient based on the result of the measurement time at sensitivity measuring microwave type concentration meter 17 can be measured by mixture concentration measuring microwave type concentration meter 18. Therefore concentration measurement of a mixture as a whole can be performed with good accuracy in a system such as the continuous mixing of multiple substances.

(Embodiment 2)

With the first embodiment, an example of the application of the present invention to a manufacturing process having a continuous mixing type substance mixing unit was described. However, with the second embodiment, an example is set forth of application to a manufacturing process in which mixing of multiple substances is performed in batches and the feedstock is supplied to the manufacturing process batch by batch.

Figure 7:
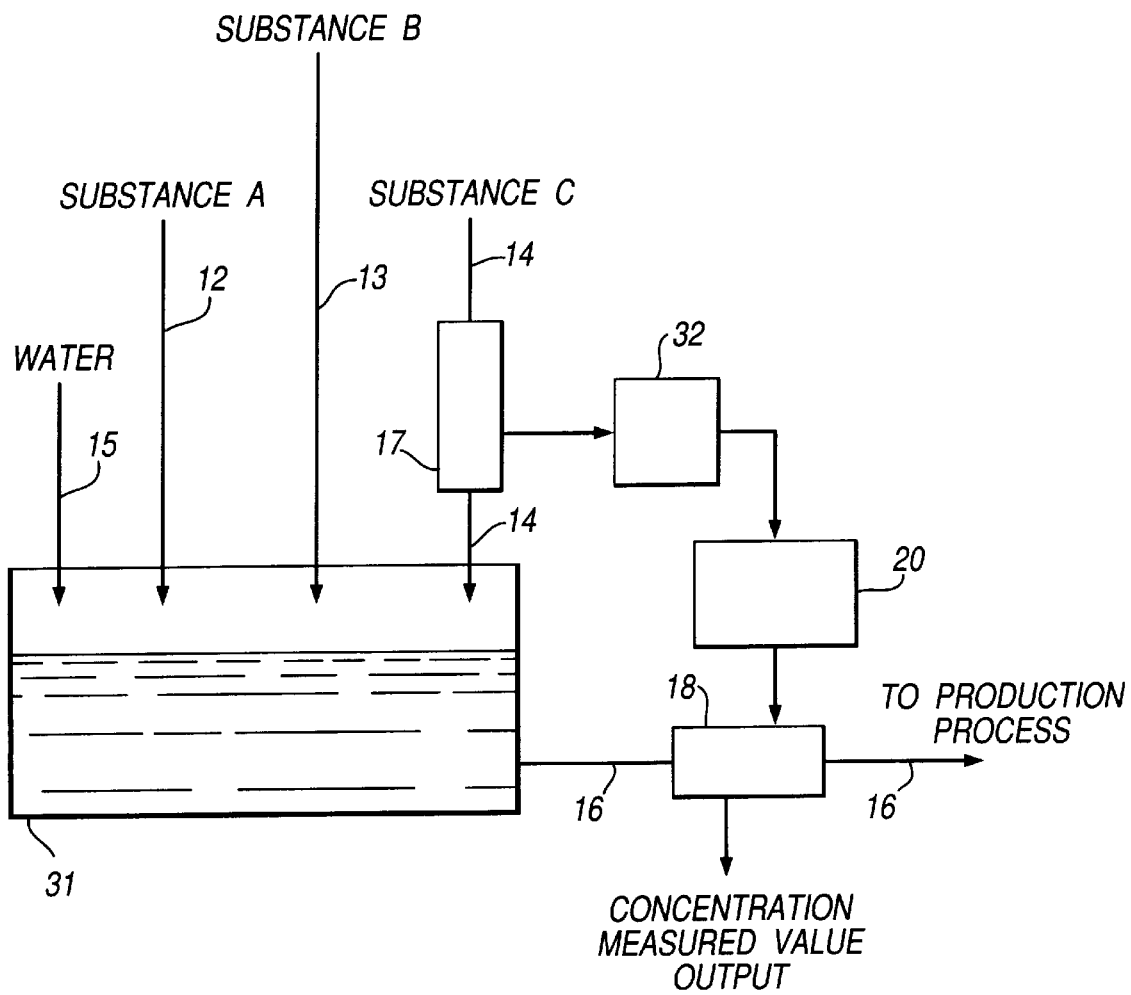
FIG. 7 is a drawing showing the schematic composition of a second embodiment of the present invention.

FIG. 7 shows the schematic composition of the second embodiment of the present invention. Parts which are identical to those in FIG. 3 have been assigned like reference numerals.

In this case, batch type mixing tank 31 is provided instead of substance mixing unit 11. Substances A, B and C, which are supplied by substance A supply pipe 12, substance B supply pipe 13 and substance C supply pipe 14 together with water from water supply pipe 15 are supplied to mixing tank 31 in constant proportions. At the same time, it is designed to prepare 1 batch of mixture by mixing. Also, the design is that 1 batch of the mixture mixed in this mixing tank 31 is supplied as feedstock to a manufacturing process (not illustrated) via mixed fluid supply pipe 16.

Sensitivity measuring microwave type concentration meter 17 is mounted on substance C supply pipe 14. Also, mixture concentration measuring microwave type concentration meter 18 is mounted on mixed fluid supply pipe 16.

Sensitivity measuring microwave type concentration meter 17 is connected to mixture concentration measuring microwave type concentration meter 18 via averaging circuit 32 and calibration curve gradient setter 20.

When 1 batch of the mixture is prepared by mixing tank 31, averaging circuit 32 calculates the measurement sensitivity of the whole of substance C that has passed through sensitivity measuring microwave type concentration meter 17 as a mean value for a certain time. It is designed to input this mean value to calibration curve gradient setter 20. Also, calibration curve gradient setter 20 sets the calibration curve gradient of mixture concentration measuring microwave type concentration meter 18. Calibration curve gradient setter 20 is provided with a computing device that calculates the relationship between the measurement sensitivity of the single substance of which the constituent composition varies (here, substance C) and the gradient of the calibration curve that finds the concentration of the mixture of substances A, B and C as a whole. Using the computing device, it finds the gradient of the calibration curve corresponding to the mean value of the measurement sensitivity of the whole of substance C that has passed through sensitivity measuring microwave type concentration meter 17. It is designed to set the obtained calibration curve gradient in mixture concentration measuring microwave type concentration meter 18.

By this means also, one batch of mixture is prepared by supplying substances A, B and C, which are supplied through substance A supply pipe 12, substance B supply pipe 13 and substance C supply pipe 14, together with water supplied from water supply pipe 15, to batch type mixing tank 31 in constant proportions and, at the same time mixing them. After that, the mixture is supplied as feedstock to a manufacturing process (not illustrated) via mixture fluid supply pipe 16.

When 1 batch of the mixture fluid is prepared in mixing tank 31, the mean value of the measurement sensitivity of the whole of substance C that has passed through sensitivity measuring microwave type concentration meter 17 is calculated by averaging circuit 32, and that mean value is inputted to calibration curve gradient setter 20. Then, a calibration curve gradient is found corresponding to the mean value of the measurement sensitivity of the whole of substance C from averaging circuit 32. This calibration curve gradient is set in mixture concentration measuring microwave type concentration meter 18, and concentration X $(=a0*\Delta\theta)$ of the mixture is found by mixture concentration measuring microwave type concentration meter 18. This concentration X is outputted as the concentration measured value.

Consequently, by this means also, the same effect can be expected as with Embodiment 1 described above. Moreover, the mean value over a certain time of the measurement sensitivity of a single substance of which the constituent composition varies is found by averaging circuit 32. The design is that the calibration curve gradient is set by calibration curve gradient setter 20 based on this mean value. Therefore the concentration measurement of the overall mixture in a manufacturing process that performs batch type mixing of multiple substances and supplies feedstock batch by batch to the manufacturing process can be performed with good accuracy.

As described above, when using the present invention, accurate concentration measurement can always be performed in the concentration measurement of the whole of a mixture in which multiple substances are mixed, even when the measurement sensitivity varies due to the variation of the constituent composition of one of these substances, without being affected by that.

Also, every time a measurement result for the measurement sensitivity of the single substance is inputted, the calibration curve gradient setting is refreshed and the most recent calibration curve setting state is maintained. Therefore highly accurate concentration measurement can be continuously performed.

Moreover, with the gradient of a calibration curve based on the result of the measurement time of the measurement sensitivity of the single substance of which the constituent composition varies, the concentration of a mixture equivalent to this measurement time can be measured. Therefore, overall concentration measurement of a mixture with a system such as continuously mixing multiple substances can be performed with good accuracy.

Furthermore, the mean value of the measurement sensitivity of a single substance of which the constituent composition varies is used in the setting of the calibration curve gradient. Therefore, by performing the mixing of multiple substances by the batch method, the overall concentration measurement of a mixture can be performed with good accuracy in a system such as supplying to a manufacturing process batch by batch.

Obviously, numerous additional modifications and variations of the present invention are possible in light of the above teachings. It is therefore to be understood that within the scope of the appended claims, the invention may be practised otherwise than as specially described therein.

What is claimed as new and desired to be secured by Letters Patent of the United States is:

1. A microwave type concentration measuring apparatus designed to find an overall concentration of a mixed fluid body stream comprising:

at least one sensitivity measurement microwave type concentration meter attached on an outer wall of a supply stream containing a single substance having a varying constituent composition for measuring a measurement sensitivity of a single substance having a varying constituent composition;

a mixed fluid body stream microwave type concentration meter attached on the outer wall of a mixed fluid body stream for measuring an uncorrected concentration of said mixed fluid body stream, wherein the mixed fluid body stream microwave type concentration meter has a means to calculate a phase lag differential between a first phase lag, $\theta_1$, of microwaves diffused by a reference liquid and a second phase lag, $\theta_2$ of microwaves which have been diffused by the mixed fluid body stream; and a calibration curve gradient setting device for setting a correction gradient for a calibration curve for the mixed fluid body stream based on the measurement sensitivity of the single substance having a varying constituent composition and the calculated phase lag differential.

2. The microwave type concentration measuring apparatus according to claim 1 wherein said calibration curve gradient setting device further comprises a computing device that calculates a relationship between said measurement sensitivity of said single substance and said phase lag differential.

3. The microwave type concentration measuring apparatus according to claim 2, further comprising:

a time lag setting device that inputs to said calibration curve gradient setting device for a specified time delay said measurement sensitivity of said single substance.

4. The microwave type concentration measuring apparatus according to claim 2, further comprising:

an averaging device which inputs to said calibration curve gradient setting device a mean value for said measurement sensitivity of said single substance.

* * * * *